(12) United States Patent
Meadows et al.

(10) Patent No.: US 7,166,303 B2
(45) Date of Patent: Jan. 23, 2007

(54) ANESTHETIC FORMULATIONS

(75) Inventors: John Meadows, Newbridge (GB); James David Du Mayne, Newbridge (GB)

(73) Assignee: Maelor Pharmaceuticals Limited, Newbridge (*) Notice: Subject to any disclaimer, the term of this patent is extended or adjusted under 35 U.S.C. 154(b) by 543 days.

(21) Appl. No.: 10/203,737

(22) PCT Filed: Feb. 28, 2001

(86) PCT No.: PCT/GB01/00868

§ 371 (c)(1),
(2), (4) Date: Oct. 31, 2002

(87) PCT Pub. No.: WO01/64187

PCT Pub. Date: Sep. 7, 2001

(65) Prior Publication Data

US 2003/0138489 A1    Jul. 24, 2003

(30) Foreign Application Priority Data

Feb. 29, 2000   (GB) .............................. 0004841.3

(51) Int. Cl.
*A61K 9/14*   (2006.01)
*A61K 9/00*   (2006.01)
*A61K 31/05*   (2006.01)

(52) U.S. Cl. ...................... 424/486; 424/400; 514/731; 514/937

(58) Field of Classification Search ................ 424/486, 424/400; 514/731, 937
See application file for complete search history.

(56) References Cited

U.S. PATENT DOCUMENTS

| 4,056,635 A | * | 11/1977 | Glen et al. ................... 514/731 |
| 5,576,012 A | | 11/1996 | Bauer et al. ................. 424/422 |
| 5,635,536 A | * | 6/1997 | Lyons ........................ 514/558 |
| 5,714,520 A | | 2/1998 | Jones et al. |
| 5,916,596 A | * | 6/1999 | Desai et al. ................. 424/489 |
| 6,264,981 B1 | * | 7/2001 | Zhang et al. ................ 424/451 |

FOREIGN PATENT DOCUMENTS

| EP | 0 796 616 A1 | 9/1997 |
| WO | WO 00/10531 | 3/2000 |

\* cited by examiner

*Primary Examiner*—Blessing Fubara
(74) *Attorney, Agent, or Firm*—Fish & Richardson P.C.

(57) ABSTRACT

Propofol solubilised in aqueous micellar preparations of poloxamers is stable at low concentrations and that such preparations are effective administration forms for Propofol.

22 Claims, 4 Drawing Sheets

ANESTHETIC FORMULATIONS

CROSS REFERENCE TO RELATED APPLICATIONS

The present application is a national phase application under 35 U.S.C. Section 371 of International Patent Application PCT/GB01/00868, filed Feb. 28, 2001, which claims priority to United Kingdom Patent Application No. 0004841.3, filed Feb. 29, 2000.

The present invention relates to novel formulations of Propofol, as well as to their use and methods of manufacture.

Propofol [2,6-bis(1-methylethyl)phenol; 2,6-diisopropylphenol] is an injectable anaesthetic first described as far back as 1956. Early preparations of Propofol were formulated with polyethoxylated castor oil. Anaphylactoid reactions were observed with these formulations, and the currently favoured formulation is a oil-in-water preparation comprising soya oil and purified egg phosphatide (marketed as Diprivan by Zeneca). The formulation of Diprivan is as follows:

| Substance | Amount | Role |
|---|---|---|
| Propofol | 10.0 mg | Active |
| Soya Bean Oil | 100.0 mg | Oil |
| Egg Lecithin | 12.0 mg | Emulsifier |
| Glycerol | 22.5 mg | Osmotic Agent |
| Sodium Hydroxide | q.s. to pH 8.5 | |
| Water | q.s. to 1.0 ml | |

Unfortunately, the presence of lecithin and soya bean oil makes Diprivan suitable as a growth medium for microorganisms, so that care must be exercised to avoid contamination of the formulation after opening the vial.

Diprivan is formulated as an oil-in-water emulsion for injection, and is widely available. However, strict aseptic techniques must be maintained when handling Diprivan, as the parenteral product contains no antimicrobial preservatives, and can support rapid growth of micro-organisms: Autoclaving is not feasible, and sterilising filters, which have pore sizes of around 0.2 μm, are not able to pass Diprivan emulsion droplets satisfactorily.

Diprivan is also associated with pain on injection, and there have been many studies to find alternative formulations. In general, these have focused on the preparation of emulsions, such as those using triglycerides, but these have tended to exhibit no particular advantage over Diprivan and suffer from similar problems, insofar as they must be prepared under strictly aseptic conditions.

There have also been studies to investigate the possibility of formulating Propofol in water using cyclodextrins. The resulting formulations show little or no pharmacological distinction over Diprivan, and suffer from the fact that the amount of cyclodextrin used must be large, as the solubility of Propofol in the formulation is dependent on one molecule of cyclodextrin complexing one molecule of Propofol. Commercially, this is somewhat prohibitive.

At room temperature, Propofol is an oil, and is not readily soluble in water. Care must be taken to thoroughly distribute Propofol in any preparation, as side effects, including embolisms, can occur if free Propofol is present in the blood stream. In relation to Propofol, the term "free", as used herein, relates to Propofol associated with the aqueous phase of a formulation, such as microdroplets of Propofol suspended therein, or the small amount that is capable of solubilising in water.

It is for this reason, amongst others, that the inclusion of water-miscible co-solvents, such as propylene glycol, within intravenous Propofol formulations, is undesirable. First, in the case of propylene glycol, undesirable medical effects, such as superficial thrombophlebitis and intravasal haemolytic reactions, have been detected following the administration of parenteral formulations. Secondly, the use of water-miscible co-solvents results in increased solubility of free Propofol within the continuous aqueous phase. For example, at ambient temperature, the solubility of Propofol in an 84% water/16% propylene glycol mixed solvent system is approximately 50% higher than for Propofol in water alone.

Accordingly, any co-solvent serving to enhance the aqueous solubility of Propofol is undesirable, as Propofol associated with the aqueous phase is associated with undesirable side effects, the least of which is acute pain on injection.

WO 00/10531 is an intermediate document, and provides microdroplet suspensions which require intense mechanical agitation or high shear to make. Such suspensions are kinetically unstable and can lead to the presence of undesirable, free Propofol.

GB-A-1,472,793 discloses the use of a range of non-ionic surfactant concentrations together with the use of an alcohol or glycol based co-solvent to solubilise a range of Propofol concentrations in aqueous systems. A poloxamer, F68, is exemplified, the formulation requiring the presence of propylene glycol in order to achieve satisfactory levels of solubilisation of Propofol. For the reasons given above, water-miscible co-solvents are associated with increased levels of free Propofol and concomitant pain on injection. In addition, this formulation cannot be sterilised by autoclaving. Furthermore, the exemplified formulation is not stable to ten fold dilution with an appropriate solvent at room temperature. This would yield undesirable free Propofol on injection.

U.S. Pat. No. 5,576,012 discloses certain new polymers used to bring compounds, such as Propofol, into solution. These polymers are not poloxamers and, furthermore, block polymers based on polyoxyethylene (PEO)/polyoxypropylene (PPO) are described therein as having very low solubilising properties and as being unsuitable for the preparation of solubilisates.

EP-A-796,616 discloses microdroplet systems which are essentially emulsions of Propofol in water, the droplets of Propofol being stabilised by the surfactant molecules at the interface between the microdroplets and the water. In this structure, the hydrophobic portion of the surfactant associates with the Propofol, while the hydrophilic portion associates with the aqueous phase, thereby stabilising the droplet. This system is associated with relatively high levels of free Propofol.

Poloxamers, which are also known as Pluronics (US) and Lutrols Europe), have been used for the solubilisation of drugs in the past. The drugs on which the poloxamers were tested either were difficult to administer by normal means, owing to their insolubility in water, or needed to be targeted, owing to their toxicity, for example.

Poloxamers, in general, are non-toxic polymeric surfactants and are poly(a-oxyethylene-b-oxypropylene-α-oxyethylene) triblock copolymers. Their solubility in water is generally good, but the properties of the individual poloxamers vary substantially. The pharmaceutical acceptability of various poloxamers is well established, with P407 and P188, in particular, being approved for parenteral administration.

There have been problems with targeting and dispensing drugs using poloxamers. Munshi, et al., [Cancer Letters, 118 (1997), 13–19] found that it was not possible for the drug to act in a normal manner, unless ultrasound was used to disrupt the micelles. The use of ultrasound in surgical techniques is not only expensive, but undesirable.

Kabanov, et al., [Journal of Controlled Release, 22 (1992), 141–158] disclose a self-assembling supramacromolecular complex comprising drug, poloxamer and antibodies to try to target the drug contained within the thus-formed complex. Targeting the micelles by incorporating antibodies is not practical for a general anaesthetic.

Rapoport, N., [Colloids and Surfaces B-Biointerfaces (1999) vol. 16, no. 1–4, 93–111] addresses Pluronic micelles as drug carriers. In particular, it notes that Pluronic micelles must be stabilised, and rules out the possibility of direct radical cross-linking of micelle cores, as this compromises drug loading capacity. A second route involves adding a small concentration of vegetable oil into dilute Pluronic solutions which, apparently, decreased micelle degradation on dilution. Introduction of any extraneous agents is undesirable in an anaesthetic formulation. The preferred route was to polymerise a temperature-responsive LCST hydrogel in the core of the Pluronic micelles.

Accordingly, there is a need for a formulation of Propofol that is readily sterilisable.

There is also a need for a formulation of Propofol that minimises free Propofol.

It has now, surprisingly, been found that micellar preparations of effective poloxamers containing Propofol are stable at low concentrations, and that such preparations are effective administration forms for Propofol.

Accordingly, in a first aspect, there is provided an aqueous, micellar poloxamer preparation comprising Propofol.

It is a particular advantage of the present invention that small amounts of pharmaceutically acceptable compounds can be used to solubilise Propofol in amounts greater than previously practicable. Thus, in preferred embodiments, water forms the major part of the formulation, by far. Further, such preparations have virtually no free Propofol to cause pain on injection. What is more, the formulations of the present invention do not appear to substantially de-micellise, even at infinite dilutions, a property which is particularly valuable for injectibles, which are effectively infinitely diluted in the blood stream.

Poloxamers are surfactants, and surfactants are amphiphilic substances. In other words, they comprise both hydrophilic and hydrophobic regions, and are commonly used to solubilise fatty substances in water. Above certain concentrations in water, surfactants tend to form micelles—agglomerations of surfactant molecules presenting their hydrophilic portions to water and internalising the hydrophobic portions. With increasing concentration, other structures may also be observed, but these tend to be somewhat complex. In the obverse, each surfactant has a minimum concentration in water below which micelles disperse (critical micelle concentration—CMC), and the aqueous surfactant preparation is effectively a solution of unimers with no structure.

Surfactant micelles are effectively envelopes and, in water, will have the more hydrophobic portion of the molecule generally forming the inside of the envelope. These micelles can readily interact with other substances and, if the substance is an oil, for example, then the substance can be entirely internalised within the micelle, or otherwise form an association, thereby effectively solubilising the substance in water.

It is undesirable for Propofol to be released as the free oil into the bloodstream, for the reasons noted above. Accordingly, using a surfactant system to solubilise Propofol in an aqueous preparation would be expected to present an unacceptable risk, with any surfactant micelles liable to disperse at lower concentrations, especially at infinite dilution, such as would be encountered on injection.

Instead, however, it has been discovered that Propofol actually encourages micelle formation of the poloxamers in water, at temperatures and concentrations lower than would otherwise be expected, and that, once the micelles contain Propofol, they remain stable at infinite dilution. Although not essential to the present invention, it is believed that Propofol is internalised within the micelle and serves to dramatically enhance the stability of the micelle. Furthermore, in vivo tests (see in vivo Test Example below) have demonstrated that the aqueous Propofol preparations of the invention are at least as effective as Diprivan, and that they show none of the side effects that would be noted if the micelles disaggregated on dilution in the bloodstream.

The nature of the poloxamer is not essential to the present invention although, especially where the formulation is intended for administration to a human, it should be pharmaceutically acceptable.

Despite the findings in the art, it has surprisingly been found that Propofol, alone, is not only sufficient to stabilise the poloxamer micelles, but that there is no requirement for the micelles to be targeted and that an extremely simple mix of Propofol, surfactant and water is sufficient to make up an anaesthetic, or sedative, formulation of the invention. Furthermore, the mix may be autoclaved without problem, and may generally be prepared by simple roller mixing, as the preparations are thermodynamically stable, and readily form.

Poloxamers are generally unreactive and non-responsive to any other additives to the system, such as BSA (Bovine Serum Albumin) or salt, such as sodium chloride. In addition, pH appears to have little, or no, effect. Thus, there is no problem with incorporating suitable substances to render the Propofol formulation suitable for injection. In particular, it is preferred that the Propofol formulation of the invention should be isotonic with the blood, so as not to cause any haemolysis, for example.

Poloxamers vary greatly in their constituent make up, and are generally characterised by the ratio of ethylene oxide units to propylene oxide units, and the molecular weight of the propylene oxide block. Within the general range of poloxamers available, it has generally been found that those having an average molecular weight of propylene oxide of greater than about 1500 D and an average percent ethylene oxide of greater than about 30% w/w are suitable. More preferably, the PPO portion is at least 2000 D while the EO portion is at least 40% w/w. However, where mixtures of poloxamers are employed, this general rule does not apply.

Where preparations of the present invention comprise a single poloxamer, then these preferably contain at least 0.8% w/w Propofol, with formulations containing 1% w/w being more preferred. The upper end of the range is generally dictated by the ability of the system to support higher concentrations of Propofol. With concentrations of 10% w/w poloxamer in water, the maximum concentration of Propofol is about 3.2% when a poloxamer such as P237 is used. Poloxamer combinations can take this even higher. However, a physiologically effective concentration is 1%, so that higher concentrations result in smaller volumes being required which can be awkward to administer. Thus, a Propofol concentration in the range of 1%–1.5% w/w is preferred.

Individually preferred poloxamers are P234, P237, P338 and P407. P188 only takes up 0.8% Propofol in a 10% aqueous solution. P407 is particularly preferred as, although it dissolves 1.7% Propofol, it has been approved for medicinal purposes. P234 and P338 are better than P407, but neither has been approved. Likewise, P237 provides excellent uptake, but also has yet to be approved.

Advantageously, combinations of poloxamers are employed in the present invention. Surprisingly, it has been found that such combinations are synergistic, where the PPO blocks have different sizes. Without being bound by theory, this is thought to be because of the formation of mixed micelles.

As noted above, poloxamers comprise PPO units and EO units. The PPO units are generally hydrophobic, and form the central portion of any micelle. In micelles with only one poloxamer, PPO blocks align with each other, while EO blocks also align with each other on the outside, to form a thermodynamically stable system. In a mixed micelle, with poloxamers of differing PPO length, when the PPO blocks of different poloxamers align, either a "hole" is left in the micellar interior, or part of the EO block of the shorter poloxamer must align with the PPO of the larger molecule. This is not thermodynamically stable and, with poloxamers that are substantially different, happens virtually not at all.

With Propofol present, these problems are overcome, and the Propofol actually encourages the formation of mixed micelles. It would appear that the Propofol compensates for the difference in PPO length, by occupying the space at the end of the shorter PPO chain, thereby obviating the need for either a thermodynamically unfavourable association of EO and PPO, or any tendency toward "holes", or both.

This ability of Propofol to stabilise mixed micelles has numerous advantages. First, it stabilises the micelle to the extent that the micelle does not disaggregate even at infinite dilution, once formed, so that no free Propofol is released. Second, the effect is sufficiently strong, that poloxamers which do not normally micellise, or are otherwise only sparingly soluble in water, readily form micelles in the presence of Propofol and another poloxamer, and vigorous mixing simply is not usually necessary. Third, the micelles are thermodynamically stable, so that they will not disaggregate on storage and, if heated to disruption, will simply reform on cooling. Fourth, synergistically formed, mixed micelles effectively actively trap Propofol, so that even less free Propofol is available in aqueous solution, thereby further reducing pain on injection. Finally, in synergistic mixtures, less poloxamer is required to solubilise 1% Propofol or, concomitantly, the same amount ensures that substantially all free Propofol is mopped up.

For example, the poloxamer known as P407 (also known as F127) has synergistic properties with P188 (also known as F68), such that the maximum concentration of Propofol able to be solubilised in a 10% w/v aqueous solution of poloxamer is at its greatest when the ratio of P407 to P188 is about 7:3 by weight. This is particularly surprising, given that a 10% w/v solution of P188 in water can only support a maximum Propofol concentration of about 0.8%, and a 10% w/v solution of P407 can support a maximum concentration of Propofol of about 1.7%, whereas the 7:3 ratio of the two poloxamers can support a maximum concentration of Propofol of about 3.5–3.8%.

Thus, in a preferred embodiment, the present invention provides an aqueous preparation of Propofol wherein the Propofol is solubilised in a synergistic mix of poloxamers.

There are preferably only two poloxamers.

The preferred concentrations of Propofol are as defined above.

As noted above, the PPO blocks of synergistic poloxamers appear to be of different weights, although it is readily determined by one skilled in the art as to which combinations of poloxamers are synergistic. Even a combination of P108 and P188 is synergistic, although P108 solubilises less than 0.1% Propofol, on its own (10% P108 in water), and may be used advantageously with P188, for example.

It appears that P401 has too little EO, and is not particularly useful in the present invention, as its lack of solubility in water is not significantly overcome by Propofol.

In general, provided that there is a difference between two poloxamers, particularly between the PPO portions, then a synergistic mixture will form. For example, a mix of P237 and P234, or a mix of P188 and P184, is not synergistic, but other mixes, such as: P407 with P338, P234, P237, P188 or P108; P338 with P234, P237, P188 or P108; P234 with P188 or P108; or P237 with P188 or P108 are all useful.

Any synergistic ratio is acceptable and useful. In general, a ratio of from about 1:1 to about 8:2 w/w is useful, with 1:1 to 7:3 being preferred.

It will be appreciated that the present invention further provides a method for the anaesthesia of a mammalian, preferably human, patient by the administration of an effective amount of a preparation of the present invention thereto.

The hydrodynamic radii of micelles of poloxamers tend not to exceed about 10–20 nm, and are readily filterable through a 0.2 μm filter. Such filters are used commercially in order to sterilise formulations, and this is a further advantage of the present invention. A major drawback with Diprivan is the lack of options for sterilisation of the formulation. It cannot be filtered through a 0.2 μm filter, as the size of the emulsion particles is generally in the region of 300 nm (0.3 μm), and the emulsion is also too unstable to be autoclaved. By contrast, the formulations of the present invention are thermodynamically stable so that they can be both filtered to sterility and/or autoclaved.

Autoclaving may be undesirable where filtering has achieved the required effect, and it should also be noted that autoclaving can have the effect of disrupting the micelles and the formulation in general, to the extent that re-mixing of the formulation may be required after autoclaving. This generally poses no particular problem because the formulations of the present invention are thermodynamically stable and, therefore, the constituents readily return to the favoured state of the formulation, although it can be inconvenient. It should also be noted that autoclaving may not be suitable if other constituents are present in the sterile formulation and which may be adversely affected by elevated temperatures.

Preparation of formulations of the present invention is generally straightforward. Although the constituents of the formulations can be added in any sequence, as desired, it will be appreciated that Propofol is virtually insoluble in water, so that the generally commercially desirable method of mixing is to prepare a poloxamer solution in water, followed by the addition of Propofol.

P407 is readily soluble in water, but heating of the water and the poloxamer, whilst mixing, can generally increase the speed of micelle formation. In addition, some poloxamers require increased temperatures in order to satisfactorily micellise in water. In general, concentrations of poloxamer of about 10% w/v are useful in the present invention, but concentrations of poloxamers, whether single or mixed, can be selected by those skilled in the art, and will generally be above 0.5% and below about 20%. More preferred concentrations are from 5 to 15%. Some poloxamers will begin to gel at higher concentrations, and any poloxamer concentration that gels at body temperature, especially when in association with Propofol, should be avoided for injection purposes. Preferred poloxamer mixes are those that enhance Propofol uptake and/or inhibit gelling, particularly at body temperature.

Propofol can be added at any stage, but it is currently preferred to add Propofol to an aqueous solution of the poloxamer. Propofol is naturally an oil, and can simply be added to the poloxamer solution and incorporated into the solution in a roller mixing technique.

The hydrodynamic size of the micelles containing Propofol does not appear to be dependent on the nature of the mixing process involved. Gentle roller mixing achieves solubilisation of the Propofol slightly more slowly than high shear mixing, but high shear mixing tends to result in foaming, and the resulting head needs to be allowed to settle before the solution can be used.

Diprivan has a Propofol concentration of about 1% w/v, and this appears to work well. Concentrations of Propofol in the formulations of the present invention are preferably formulated to contain an amount of Propofol to be about the equivalent of the Diprivan formulation, and it has been established that formulations of the present invention containing 1% Propofol have similar pharmacological properties to Diprivan. Lower concentrations of Propofol require the administration of concomitantly greater volumes of the formulation of the invention, while higher concentrations need to be handled with greater care. Thus, Propofol concentrations in the range of about 0.5 to about 2% are generally preferred, with about 1% being most preferred.

Formulations of the present invention are easily prepared at a fraction of the cost of the manufacture of Diprivan; they can be sterilised after preparation; they have no constituents which encourage the multiplication of micro-organisms in the formulation; and they are substantially stable, all of which properties are in direct contrast to Diprivan.

The formulations of the present invention need very few constituents. Propofol, surfactant and water is sufficient for a basic formulation, but it is greatly preferred that any injectable formulation is made up with saline, for example, in order to render the formulation isotonic, or iso-osmotic, with blood. In the preparations of the present invention, an appropriate level is about 0.45%, in order to achieve an osmolality of about 300 mOsm, with a range of about 280–320 mOsm being generally desirable. Anything outside of this range may be used, but may possibly lead to perceptible pain.

Apart from the desirability of rendering the formulation isotonic with blood, it is generally preferred to minimise the number of other ingredients and to ensure that any formulation passed on to the patient is sterile. Given that the formulation can be sterilised after preparation and that simple preparations of the invention do not readily support growth of micro-organisms, then this is not a problem. Nevertheless, if it is desired to incorporate sterilising agents, stabilising agents, or bacteriostats, for example, then this can be done, and prior art formulations of Propofol have included sodium metabisulphite and EDTA (ethylene diamine tetraacetic acid), which may be incorporated in the formulations of the present invention, if desired.

It will be readily appreciated by those skilled in the art how to administer formulations of the present invention to a human or animal. Less Propofol is generally required with increasing age but, in general, there appears to be no particular effect of sex or body mass on the overall requirement of Propofol, and that amounts of Propofol in the region of 1.5 mg/kg to about 2.5 mg/kg is generally sufficient for the induction of general anaesthesia, whilst long term infusion for anaesthesia requires a dose of about 4–12 mg/kg per hour, the maximum effect being within about one minute of dosing and duration of action being about 5 to 10 minutes after administration. Lower consistent doses can provide sedation. The formulations of the present invention are generally intended for administration to the patient by parenteral injection, but other forms of administration, such as via a catheter, provide a similar effect. In general, administration into a relatively large vein is preferred, in order to minimise any pain.

The formulations of the present invention can be provided in any suitable form and may be provided in any suitable containers appropriate to maintaining sterility. If necessary, the containers may be autoclaved immediately prior to use, although this is not preferred, and is not generally convenient.

The formulations of the present invention may also be provided as concentrates, although high concentrations of surfactants are generally not preferred and, in the case of certain poloxamers, can lead to gelation which is undesirable. Accordingly, it is generally preferred that the formulations of the present invention are provided in a form suitable for direct injection. In such a capacity, any ampoule (for example) containing the formulation of the invention may, as appropriate, be used directly in a suitably adapted syringe to administer the formulation.

More generally, the ampoule, or other container, may be pierceable, or have a removable seal or cap, such that a syringe may be used to extract the solution, or the solution may be pourable directly into a syringe, or other apparatus for dosing the patient.

Figure 1:
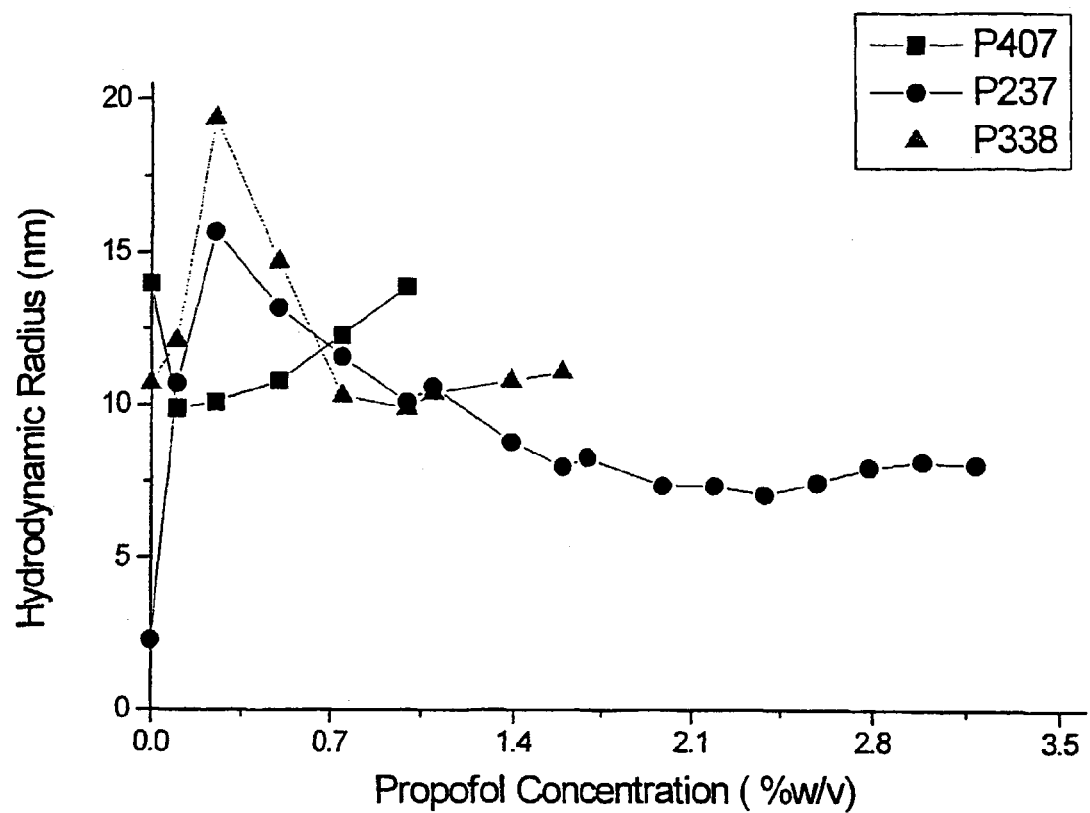
FIG. 1 shows the effect of sequential dilution on the aqueous hydrodynamic sizes of the micelles in an initially 10% w/v aqueous P407 solution containing either no or 1.0% w/v solubilised Propofol.

The present invention will now be illustrated with respect to the following, non-limiting Examples in which, unless otherwise stated, all percentages are weight by volume and water used is sterile, deionised water.

EXAMPLE 1

Preparation of Samples

Poloxamer Stock Solutions (500 ml):

10% w/v poloxamer solutions were prepared by adding 50 g of poloxamer, or poloxamer mix, to 350 ml of distilled water. This was then mixed using an overhead stirrer until completely dissolved. This solution was then made up to 500 ml with distilled water.

Propofol Formulations (20 ml):

1% w/w Propofol formulations were prepared by adding 0.2 g of Propofol to 20 ml of a stock solution, as prepared above. The solutions were then placed on a roller mixer to mix until all the Propofol had been solubilised (determined by visual evaluation), usually overnight, or for a sufficiently long period of time, sometimes up to 72 hours. Unless otherwise indicated, this was the method employed in all subsequent Examples for mixing in Propofol.

EXAMPLE 2

Solubilisation of Propofol in Aqueous Poloxamer Solutions

Propofol formulations were also prepared by mixing using a high shear mixer for approximately 5 minutes. Although this increased the rate of solubilisation of Propofol, it required larger working volumes and time had to be allowed for the foam formed during mixing to collapse before use.

Poloxamer P407 was used as a solubilising agent for Propofol in aqueous based formulations. It was found that optically clear solutions containing 1% w/v Propofol in 10% w/v P407 could be prepared by either simple roller mixing or high shear mixing. The hydrodynamic size of the poloxamer micelles was assessed using the Oros, Dynapro 801 Dynamic Light Scattering/Molecular Sizing Instrument, and the results are shown in Table 1 below.

TABLE 1

High Shear vs. Roller Mixing

| Mixing Method | P407 Conc. (% w/v) | Propofol Conc. (% w/v) | Temperature (° C.) | Hydro-dynamic Radius (nm) |
|---|---|---|---|---|
| High Shear | 10 | 1.0 | 22 | 10 |
| Roller | 10 | 1.0 | 22 | 11 |

Solubilisation of Propofol into aqueous poloxamer solution occurs spontaneously upon gentle agitation. The fact that stable homogeneous systems can be prepared using such gentle agitation is indicative that the incorporation of Propofol into the aqueous system is through a mechanism of solubilisation into poloxamer micelles rather than through any emulsification mechanism. Micellar solubilisation, such as the incorporation of Propofol into P407 micelles, results in a thermodynamically stable system. It is energetically favourable for this type of system to form so only gentle agitation is required to facilitate adequate contact between the solubilising vehicle and the solubilised species. In contrast, most emulsions can be classed as kinetically stable systems. With such systems, sufficient energy must be applied to overcome a significant activation energy before they can form; this energy is usually applied through some form of high shear mixing. Similarly, once formed, there is a significant activation energy barrier to any de-emulsification process, although these systems may be broken, given sufficient time or the input of sufficient energy, e.g. centrifugation. Although kinetically stable systems can remain stable for a long time, thermodynamically stable systems, such as those of the present invention, have, technically, infinite long-term stability.

EXAMPLE 3

Maximum Propofol Concentrations in Poloxamer Solutions

In order to determine the maximum additive concentration (MAC) of Propofol in surfactant systems, the appropriate amount of Propofol was added to 30 ml of the stock solution and mixed as described in Example 1 until Propofol was solubilised, or until it was apparent that that amount of Propofol could not be solubilised. Ten ml aliquots were taken from samples in which Propofol had been completely solubilised, for particle size analysis. The concentration of Propofol in the remaining solution was increased by adding the appropriate amount of Propofol and mixing as above. This process was repeated for each poloxamer/surfactant solution until the maximum additive concentration MAC) of Propofol was determined.

Table 2 below shows the results for the determination of the maximum additive concentration (MAC) for Propofol in the poloxamer solutions studied.

TABLE 2

MAC for Propofol in a Number of Poloxamer solutions at 10% w/v at 25° C.

| Poloxamer | Composition | % w/w PPO | % w/w PEO | MAC* (% w/v) |
|---|---|---|---|---|
| P124 | PO 21 Units, EO 14 Units | 60 | 40 | <0.1% |
| P188 | PO 30 Units, EO 120 Units | 20 | 80 | 0.8% |
| P237 | PO 39 Units, EO 156 Units | 30 | 70 | 3.2–3.3% |
| P338 | PO 56 Units, EO 224 Units | 20 | 80 | 2.0–2.2% |
| P407 | PO 57 Units, EO 196 Units | 30 | 70 | 1.5–1.7% |

*MAC: the lowest figure represents the highest amount of Propofol deemed to be fully solubilised i.e. optically clear; the higher figure represents the lowest concentration of Propofol deemed not to be fully solubilised There appears to be no obvious correlation between poloxamer structure in terms of % PO and PPO block length, and MAC. Studies of 5% w/v poloxamer solutions have shown that P124 and P188 do not micellise until 40° C. and 57° C. respectively and, so, are not present as micelles in aqueous solution at room temperature. However, the above results indicate that the presence of Propofol in P188 systems induces micelle formation at room temperature. Similarly, where P237 at 5% w/v has been shown to micellise at around 34° C., the presence of Propofol appears to induce micellisation at room temperature, hence enabling it to solubilise large amounts of Propofol.

Table 2a shows the results of a separate set of experiments (MAC of Propofol in 10% w/w aqueous solutions of various poloxamers with simple roller mixing at room temperature).

TABLE 2a

| Poloxamer | MAC (% w/w) |
|---|---|
| P237 | 3.2 |
| P338 | 2.2 |
| P407 | 1.7 |
| P188 | 0.8 |
| P234 | 2.0 |
| P401 | 0.1 |
| P184 | 0.1 |
| P124 | <0.1 |
| P108 | <0.1 |

The nomenclature used for the "P" poloxamers in this Example, and generally herein, is such that the first two figures, when multiplied by 100, represent the average molecular weight of the PPO block, whilst the last figure, when multiplied by 10, represents the ethylene oxide content (% w/w) of the poloxamer. Thus, for P407, the average molecular weight of the PPO block is 4000 Daltons with a 70% w/w/ethylene oxide content.

It can be seen that, with a PPO of less than 2000 D, or an EO of less than 40%, then a 10% w/w aqueous solution of the poloxamer essentially becomes incapable of supporting a solution of 1% Propofol.

EXAMPLE 4

Solubility of Propofol in Water

Analyses were performed using the Perkin Elmer Lambda 5 UV/Vis Spectrophotometer.

Two sets of standards were prepared by serial dilution of:
1. 10% poloxamer P407/1% Propofol solution in water.
2. 1% Propofol solution in ethanol (EtOH).

Dilutions were performed with water and EtOH respectively. The standards were further diluted one hundred fold prior to measurement of their UV absorption spectra recorded.

The wavelength of maximum absorption ($\lambda_{max}$) for Propofol is around 272 nm and was unchanged for a 1% solution in ethanol, a 1% solution in 10% P407 in water, or a saturated aqueous solution. Graphs for both the ethanol and poloxamer solutions are linear up to Propofol concentrations of 0.02% w/v. Using these, it was possible to estimate the concentration of Propofol in a saturated aqueous solution as approximately $1\times10^{-3}$ M.

EXAMPLE 5

Effect of Propofol on the Micellisation/Demicellisation Behaviour of Poloxamers

Accompanying FIG. 1 shows the effect of sequential dilution on the aqueous hydrodynamic sizes of the micelles in an initially 10% w/v aqueous P407 solution containing either no or 1.0% w/v solubilised Propofol. The results indicate that micelles are present in the Propofol system at concentrations beneath which P407 would only usually exist as unimers. The presence of micelles was supported by visual evaluation of the samples. Any Propofol present in these systems remained solubilised, as none was observed on the surface of the samples, which would be expected if micellar disaggregation had occurred. This suggests that Propofol is acting as a preferential solvent for the PPO segments, thereby precluding micellar disaggregation. An affinity between PPO and Propofol is likely to make demicellisation thermodynamically less favourable. As noted above, the presence of Propofol in P237 and P188 systems induces micellisation at room temperature, whereas simple, 5.0% w/v aqueous solutions of P237 and P188 do not micellise until 34° C. and 57° C. respectively.

EXAMPLE 6

Figure 2:
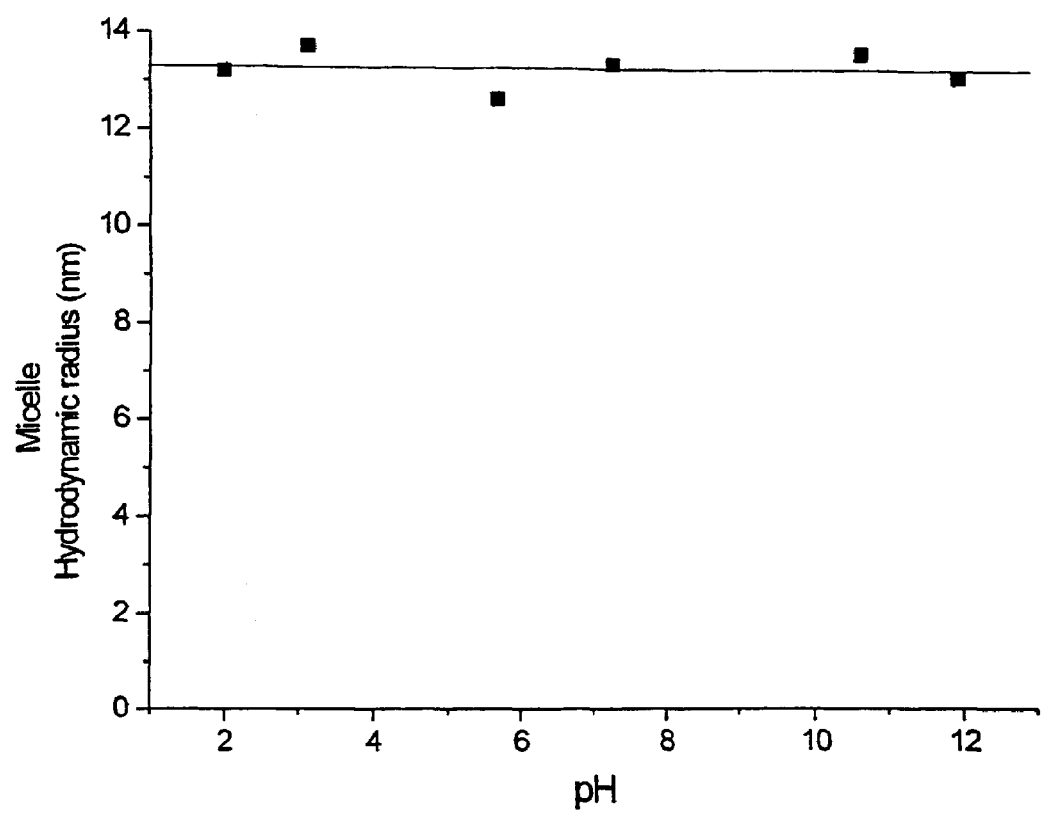
FIG. 2 shows the influence of pH on the hydrodynamic radii of P407 micelles (10% w/v in water) containing 1% solubilised Propofol.
Figure 3:
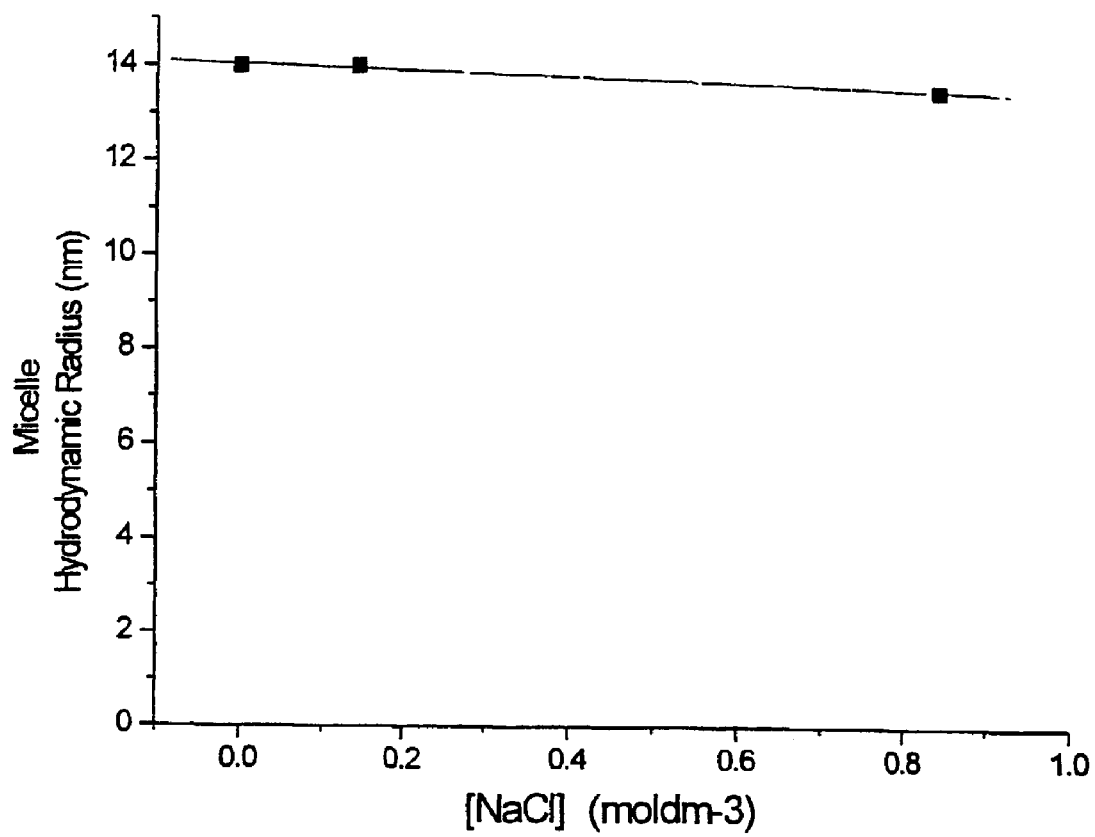
FIG. 3 shows the influence of added electrolyte (NaCl) on the hydrodynamic radii of P407 micelles (10% w/v in water) containing 1% solubilised Propofol.

Formulation Stability a) The influences of pH and added electrolyte (NaCl) on the hydrodynamic radii of P407 micelles (10% w/v in water) containing 1% solubilised Propofol are shown in FIGS. 2 and 3, respectively.

It can be seen that the hydrodynamic radius of the micelles in the system is not affected by the presence of salt or by changes in formulation pH, as the hydrodynamic radii (13–15 nm) are still within the normal size range of the micelles in the system, ca. 14 nm. The essential independence of micelle size with pH and ionic strength can be taken as a reflection of the non-ionic nature of both poloxamer and Propofol molecules.

b) In order to provide a preliminary assessment of the physical stability of poloxamer formulations of the present invention upon intravenous injection, the effect of the addition of the globular protein bovine serum albumin (BSA) on the hydrodynamic radii of a 10% P407, 1% Propofol formulation was investigated. The results are shown in FIG. 4.

Figure 4:
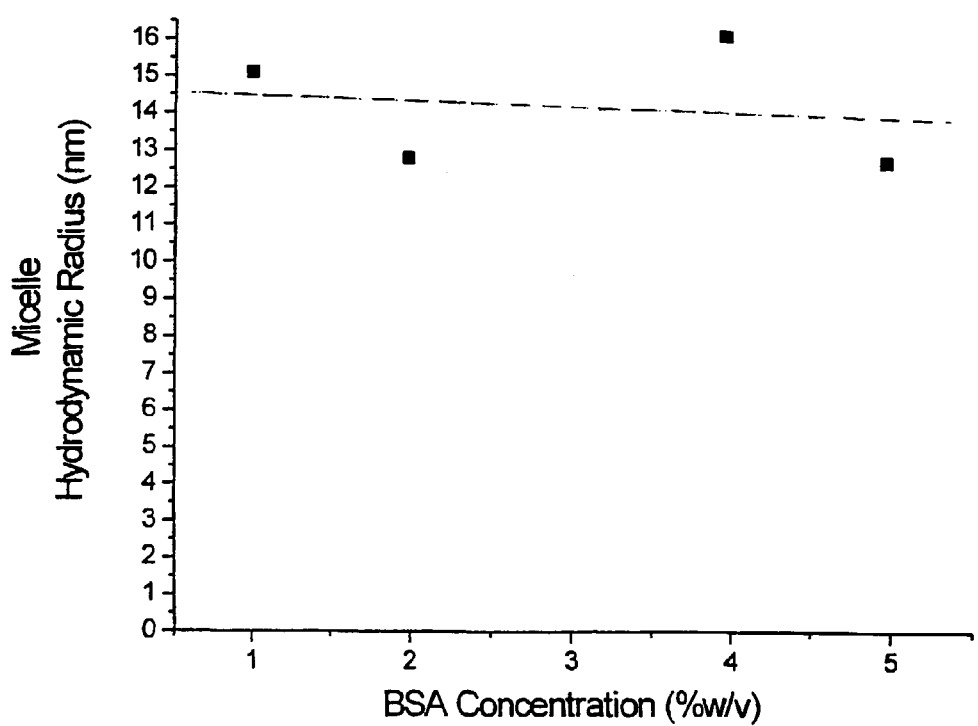
FIG. 4 shows the effect of the addition of the globular protein bovine serum albumin (BSA) on the hydrodynamic radii of a 10% P407, 1% Propofol formulation.

FIG. 4 indicates that the hydrodynamic radii of the Propofol-containing micelles were essentially independent of the addition of BSA, which suggests that there is no strong interaction between the protein and the poloxamer micelles.

EXAMPLE 7

Mixed Poloxamer Systems

The MAC values of Propofol in various mixed poloxamer systems, at a total poloxamer concentration of 10% w/w, are shown in Table 3, below. All values are in % w/w.

TABLE 3

| Poloxamer A | Poloxamer B | MAC Propofol | Pro rata MAC | Poloxamer A | Poloxamer B | MAC Propofol | Pro rata MAC |
|---|---|---|---|---|---|---|---|
| P338 | P188 | | | P407 | P188 | | |
| 10 | 0 | 2.2 | 2.2 | 10 | 0 | 1.7 | 1.7 |
| 7 | 3 | 2.2 | 1.8 | 7 | 3 | 3.5 | 1.4 |
| 3 | 7 | 1.8 | 1.2 | 3 | 7 | 2.75 | 1.1 |
| 0 | 10 | 0.8 | 0.8 | 0 | 10 | 0.8 | 0.8 |
| P234 | P237 | | | P407 | P237 | | |
| 10 | 0 | 2 | 2 | 10 | 0 | 1.7 | 1.7 |
| 7 | 3 | 1.7 | 2.4 | 7 | 3 | 3.2 | 2 |
| 3 | 7 | 1.9 | 2.8 | 3 | 7 | 3.2 | 2.5 |
| 0 | 10 | 3.2 | 3.2 | 0 | 10 | 3.2 | 3.2 |

TABLE 3-continued

| Poloxamer A | Poloxamer B | MAC Propofol | Pro rata MAC | Poloxamer A | Poloxamer B | MAC Propofol | Pro rata MAC |
|---|---|---|---|---|---|---|---|
| P188 | P184 | | | P401 | P108 | | |
| 10 | 0 | 0.8 | 0.8 | 10 | 0 | <0.1 | <0.1 |
| 7 | 3 | <0.8 | 0.7 | 7 | 3 | <0.1 | <0.1 |
| 3 | 7 | <0.8 | 0.6 | 3 | 7 | <0.1 | <0.1 |
| 0 | 10 | <0.5 | <0.5 | 0 | 10 | <0.1 | <0.1 |
| P401 | P407 | | | P108 | P188 | | |
| 10 | 0 | <0.1 | <0.1 | 10 | 0 | <0.1 | <0.1 |
| 7 | 3 | <0.1 | 0.5 | 7 | 3 | 0.4 | 0.2 |
| 3 | 7 | <0.1 | 1.2 | 3 | 7 | 1 | 0.6 |
| 0 | 10 | 1.7 | 1.7 | 0 | 10 | 0.8 | 0.8 |
| P188 | P237 | | | | | | |
| 10 | 0 | 0.8 | 0.8 | | | | |
| 7 | 3 | 2 | 1.5 | | | | |
| 3 | 7 | 2 | 2.5 | | | | |
| 0 | 10 | 3.2 | 3.2 | | | | |

Synergy is established when the experimentally determined MAC for the mixed systems is greater than the value calculated from the pro rata addition of the solubilisation capacity of each of the Poloxamer components individually. These pro rata values are included in the table for comparison.

Example calculation: P407/P188 mixtures
MAC 10% P407=1.7% MAC 10% P 188=0.8%

$$\text{Pro rata MAC for 7\% P 407/3\% P 188} = (0.7 \times 1.7) + (0.3 \times 0.8)$$
$$= 1.19 + 0.24$$
$$= 1.4\%$$

Similarly for 3% P407/7% P188, Pro rata MAC=1.1%

Accordingly, synergy in the above Table 3 is demonstrated by the mixtures: P407/P188; P407/P237; P338/P188 and P188/P108. The dissimilarity in the PPO block lengths of the mixtures is notable.

The mixtures: P234/P237; P188/P184; P401/P407; and P401/P108 displayed no evidence of synergy. The similar PPO block lengths of the mixtures is notable, except for P401/P108. In this case, P401 is essentially insoluble in water at room temperature, and this does not appear to be counteracted by P108.

In vivo Test Example

A study was performed to compare the anaesthetic effects of a Propofol formulation of the invention with the commercially available Diprivan emulsion, by assessing sleeping time after intravenous administration to male Wistar rats. Both formulations contained 1% Propofol. The test formulation was an aqueous preparation of 0.9% saline containing 10% poloxamer (8% P407/2% P188) and 1% Propofol which, after mixing, was passed through a 0.2 µm filter for sterilisation. Fresh 20 ml vials of Diprivan were used for the comparison.

The test formulation and Diprivan emulsion were administered by a single intravenous injection at doses of 10, 15 and 20 mg/kg at a rate of 1 ml/kg/10 seconds. The onset of sleep and duration of sleeping time of each rat were recorded. One minute after the completion of dosing, the respiratory rate was measured over a 20-second period. The intervals between righting and walking and righting and co-ordination (normal gait) were also recorded.

Experimental

The test formulation and Diprivan emulsion were administered intravenously via a tail vein at a rate of 1 ml/kg/10 seconds.

The treatment groups employed for the study were as follows:

| Group | Intravenous treatment | Dose (mg/kg) |
|---|---|---|
| 1 | Test formulation | 10 |
| 2 | Test formulation | 15 |
| 3 | Test formulation | 20 |
| 4 | Diprivan | 10 |
| 5 | Diprivan | 15 |
| 6 | Diprivan | 20 |

Immediately after intravenous administration, the rats were placed in a constant temperature environment (approximately 32° C.). The time to onset of sleep (loss of righting reflex) and the duration of the sleeping time of each rat (as indicated by the time taken for the reappearance of the righting reflex) were recorded. One minute after loss of righting reflex, the respiratory rate was recorded over a 20-second period. The intervals between righting and walking and between righting and co-ordination (normal gait) were also recorded.

The sleeping times, respiration rates and recovery times for the animals dosed with test formulation were compared with those of the same dose level of Diprivan using Student's t test.

The results are shown in Tables 4 and 5.

TABLE 4

Effects of intravenous administration of a test formulation on sleeping time

| Group | Intravenous treatment | Dose (mg/kg) | Mean sleeping time (minutes ± sd) |
|---|---|---|---|
| 1 | A test formulation in saline | 10 | 7.3 ± 0.86 |
| 2 | A test formulation in saline | 15 | 10.4 ± 1.54 |
| 3 | A test formulation in saline | 20 | 14.3 ± 2.86 |
| 4 | Diprivan | 10 | 7.9 ± 1.52 |
| 5 | Diprivan | 15 | 10.7 ± 2.04 |
| 6 | Diprivan | 20 | 16.3 ± 2.20 | sd standard deviation

TABLE 5

Effects of intravenous administration of a test formulation on walking, co-ordination and respiration time

| | | | Difference in time (min ± sd) between regain of righting reflex and: | | Respiration rate |
|---|---|---|---|---|---|
| Group | Intravenous treatment | Dose (mg/kg) | Walking | Co-ordination (normal gait) | over a 1 minute period (± sd) |
| 1 | A test formulation in saline | 10 | 0.8 ± 0.91 | 4.2 ± 0.89 | 115.2 ± 11.33 |
| 2 | A test formulation in saline | 15 | 0.5 ± 0.37 | 4.0 ± 1.00 | 117.3 ± 10.05 |
| 3 | A test formulation in saline | 20 | 0.5 ± 0.27 | 4.6 ± 1.10 | 102.3 ± 18.68 |
| 4 | Diprivan | 10 | 0.5 ± 0.38 | 4.0 ± 1.28 | 120.6 ± 10.08 |
| 5 | Diprivan | 15 | 0.6 ± 0.42 | 3.9 ± 1.43 | 115.8 ± 9.92 |
| 6 | Diprivan | 20 | 0.3 ± 0.27 | 4.5 ± 1.43 | 101.1 ± 12.97 | sd standard deviation

Study

The sleeping times, respiration rates and recovery times (time to walking and co-ordination) of animals treated with the test formulation at intravenous doses of 10, 15 and 20 mg/kg, were very similar to those of animals treated with Diprivan at the same doses. There were no statistically significant differences between the two formulations of Propofol in any of the parameters measured.

Accordingly, it has been demonstrated that Propofol formulations of the invention, which are easy and inexpensive to prepare, and which are readily sterilisable and stable, have directly comparable pharmacological characteristics to those of Diprivan.

The invention claimed is:

1. An aqueous preparation of Propofol, wherein the Propofol is solubilised in a synergistic mix of poloxamers, the poloxamers being in a ratio from 7:3 to 3:7 w/w, and the synergistic mix being: P407 with P237; P407 with P188; or P338 with P188.

2. A preparation according to claim 1, wherein the total poloxamer concentration is above 0.5% and below 20% w/w.

3. A preparation according to claim 2, wherein the poloxamer total concentration is between 6 and 14% w/v.

4. A preparation according to claim 3, wherein the poloxamer total concentration is between 8 and 12% w/v.

5. A preparation according to claim 3, wherein the poloxamer total concentration is about 10% w/w.

6. A preparation according to claim 1, wherein the poloxamers are P407 and P188 in a ratio to each other of about 7:3 by weight, respectively.

7. A preparation according to claim 1, comprising at least 1% w/w Propofol.

8. A preparation according to claim 1, which does not demicellise at infinite dilution.

9. A preparation according to claim 1, which is isotonic with blood.

10. A preparation according to claim 1, consisting of Propofol, poloxamers and water.

11. A preparation according to claim 1, consisting of Propofol, poloxamers and saline.

12. A preparation according to claim 1, further comprising at least one constituent selected from the group consisting of sterilising agents, stabilising agents, and bacteriostats.

13. A preparation according to claim 1, wherein the synergistic mix is P338 with P188.

14. A preparation according to claim 1, wherein the synergistic mix is P407 with P188.

15. A preparation according to claim 1, wherein the synergistic mix is P407 with P237.

16. A preparation according to claim 13, wherein the total poloxamer concentration is above 0.5% and below 20% w/w.

17. A preparation according to claim 14, wherein the total poloxamer concentration is above 0.5% and below 20% w/w.

18. A preparation according to claim 15, wherein the total poloxamer concentration is above 0.5% and below 20% w/w.

19. A preparation according to claim 16, wherein the poloxamer total concentration is between 6 and 14% w/w.

20. A preparation according to claim 17, wherein the poloxamer total concentration is between 6 and 14% w/w.

21. A preparation according to claim 18, wherein the poloxamer total concentration is between 6 and 14% w/w.

22. An aqueous preparation of Propofol, wherein the Propofol is solubilised in a synergistic mixture of two poloxamers, the poloxamers being in ratio from 7:3 to 3:7 w/w, and the PPO sizes of the poloxamers differing by 500 Daltons or more.

* * * * *